United States Patent
Giese et al.

(10) Patent No.: US 10,161,933 B2
(45) Date of Patent: Dec. 25, 2018

(54) CATIONIC TAGS FOR ATTOMOLE LEVEL DETECTION OF ANALYTES BY MASS SPECTROMETRY

(71) Applicants: Roger Giese, Hanover, MA (US); Poguang Wang, Westborough, MA (US)

(72) Inventors: Roger Giese, Hanover, MA (US); Poguang Wang, Westborough, MA (US)

( * ) Notice: Subject to any disclaimer, the term of this patent is extended or adjusted under 35 U.S.C. 154(b) by 0 days.

(21) Appl. No.: 16/021,941

(22) Filed: Jun. 28, 2018

(65) Prior Publication Data
US 2018/0321226 A1 Nov. 8, 2018

Related U.S. Application Data

(62) Division of application No. 15/547,588, filed as application No. PCT/US2016/016022 on Feb. 1, 2016, now Pat. No. 10,036,743.

(Continued)

(51) Int. Cl.
*G01N 33/52* (2006.01)
*G01N 24/00* (2006.01)
(Continued)

(52) U.S. Cl.
CPC ........... *G01N 33/52* (2013.01); *C07C 217/48* (2013.01); *C07C 217/58* (2013.01); *G01N 2458/15* (2013.01); *G01N 2560/00* (2013.01)

(58) Field of Classification Search
CPC ............... G01N 33/52; G01N 2458/15; G01N 2560/00
See application file for complete search history.

(56) References Cited

U.S. PATENT DOCUMENTS

| | | | |
|---|---|---|---|
| 6,623,928 B2* | 9/2003 | Van Ness | C07D 211/78 435/6.1 |
| 2004/0157344 A1* | 8/2004 | Wang | G01N 33/6848 436/518 |

(Continued)

OTHER PUBLICATIONS

P. Wang et al., "Cationic Xylene Tag for Increasing Sensitivity in Mass Spectrometry", J. Am. Soc. Mass Spectrom., Jun. 27, 2015, vol. 26, pp. 1713-1721.

*Primary Examiner* — Nicole Ippolito
*Assistant Examiner* — Sean Luck
(74) *Attorney, Agent, or Firm* — Posternak Blankstein & Lund LLP

(57) ABSTRACT

The invention provides methods of detecting an analyte by multi-stage mass spectrometry with improved S/N ratio. An analyte is labeled with a positively-charged mass tag to form a precursor ion that leads by anchimeric assistance to a greatly enhanced, analyte-characteristic first product ion that can, in turn, lead to a greatly enhanced, analyte-characteristic second product ion in a mass spectrometer. Either a three stage mass spectrometer (true MS3) or a two-stage mass spectrometer (MS2) operated in a pseudo MS3 mode can be used. The precursor ion is split via an anchimeric-assisted reaction to form a first product ion, which in turn can be fragmented to form the second product ion. The methods offer extreme ultrasensitivity, at the low amol level. The invention also provides anchimeric mass tags for use in the methods. A wide variety of previously undetectable analytes of biological or environmental origin can be detected and quantified.

19 Claims, 14 Drawing Sheets

Related U.S. Application Data

(60) Provisional application No. 62/111,987, filed on Feb. 4, 2015, provisional application No. 62/110,008, filed on Jan. 30, 2015.

(51) Int. Cl.
*C07C 217/58* (2006.01)
*C07C 217/48* (2006.01)

(56) References Cited

U.S. PATENT DOCUMENTS

2010/0255607 A1* 10/2010 Giese ............... G01N 33/5306
                                                        436/501
2011/0294153 A1* 12/2011 Gelb ................... C07D 213/20
                                                        435/29

* cited by examiner

| | Standard Mixture of Phenols | m/z |
|---|---|---|
| 1 | phenol | 298.217 |
| 2 | o-cresol | 312.233 |
| 3 | 2,4-dimethylphenol | 326.248 |
| 4 | 2-chlorophenol | 332.178 |
| 5 | 2-nitrophenol | 343.202 |
| 6 | 4-nitrophenol | 343.202 |
| 7 | 4-chloro-3-methylphenol | 346.194 |
| 8 | 2,4-dichlorophenol | 366.139 |
| 9 | 2,4-dinitrophenol | 388.187 |
| 10 | 2,4,6-trichlorophenol | 400.100 |
| 11 | 2-methyl-4,6-dinitrophenol | 402.203 |
| 12 | pentachlorophenol | 468.022 |

*Fig. 8A*

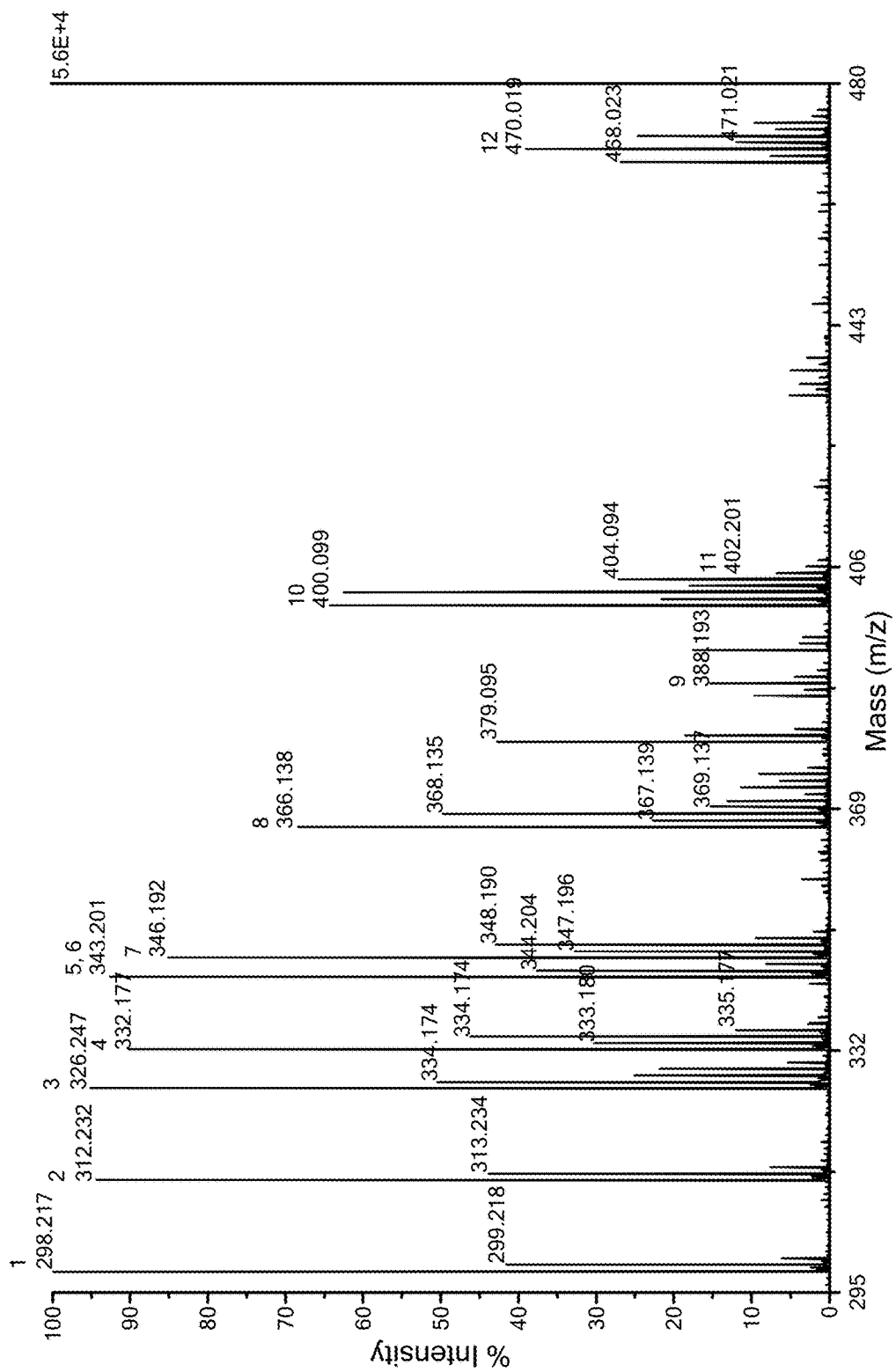

CATIONIC TAGS FOR ATTOMOLE LEVEL DETECTION OF ANALYTES BY MASS SPECTROMETRY

STATEMENT REGARDING FEDERALLY SPONSORED RESEARCH OR DEVELOPMENT

The invention was developed with financial support from Grant No. P42ES017198 from the National Institute of Environmental Health Sciences. The U.S. Government has certain rights in the invention.

BACKGROUND

Mass spectrometry (MS) is a powerful and common detection technique because it can provide both high specificity and sensitivity for many analytes. However, when detection of an analyte of interest is not particularly sensitive by this technique, usually due to an insufficient signal-to-noise (S/N) ratio, MS can fail to provide detection. This problem can sometimes be overcome by reacting an otherwise undetectable analyte with a molecular tag that boosts sensitivity, such as an intensified neutral loss tag. See Wang, P., Li, G., Gao, J., Giese, R. W., Xin, Z. Intensified Neutral Loss Tags and their Use Thereof in Mass Spectrometry; U.S. Pat. No. 7,556,969B, Jul. 7, 2009; and U.S. Pat. No. 7,947,511B2, May 24, 2011. However, current tags for mass spectrometry do not meet all detection needs.

SUMMARY OF THE INVENTION

The invention provides methods of detecting or quantifying an analyte with improved S/N ratio. In methods of the invention, an analyte is labeled with a quaternary amine or other positively-charged mass tag to form a precursor ion that leads by anchimeric assistance to a greatly enhanced, analyte-characteristic first product ion that can, in turn, lead to a greatly enhanced, analyte-characteristic second product ion in a mass spectrometer. Either a three stage mass spectrometer (true MS3) or a two-stage mass spectrometer (MS2) operated in a pseudo MS3 mode can be used. The precursor ion is split via an anchimeric-assisted reaction to form a first product ion, which in turn is fragmented to form the second product ion. The methods offer extreme ultra-sensitivity, at the low amol level. The invention also provides anchimeric mass tags for use in the methods.

One aspect of the invention is a method for detecting an analyte A using a multi-stage mass spectrometer having at least first and second stages. The method include the steps of: (a) contacting a sample containing the analyte with a molecular tag $Q^+$, whereby the analyte is covalently labeled with the molecular tag to produce tagged analyte $Q^+$-A, (b) subjecting $Q^+$-A to volatization into the gas phase and then filtration in the first stage; (c) subjecting $Q^+$-A to cleavage by energetic activation to form a resonance-stabilized first product ion $q^+$-A and a neutral amine, wherein $q^+$ and the neutral amine are both fragments of $Q^+$; (d) filtering $q^+$-A in the second stage; and (e) detecting $q^+$-A in a manner typical for mass spectrometry.

In the method described above, $Q^+$ is represented by Formula (I):

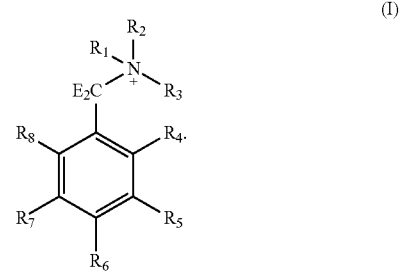

(I)

$R_1$, $R_2$, and $R_3$ are each independently selected from methyl, ethyl, propyl, cyclopropyl, isopropyl, butyl, fluoromethyl, difluoromethyl, trifluoromethyl, fluoroethyl, difluoroethyl, trifluoroethyl, cyanomethyl, cyanoethyl, hydroxyethyl, methoxyethyl, and nitroethyl, and each E is independently hydrogen or deuterium. One of $R_4$-$R_8$ bears a reactivity group that enables $Q^+$ to be attached covalently to the analyte to form $Q^+$-A, and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof. $Q^+$-A contains at least one O, N or S atom, which is separated from the C atom of the $CE_2NR_1R_2R_3$ substituent by four or five single or double bonds. The O, N or S atom is part of the $R_4$ group.

In another embodiment of the method described above, $Q^+$ has a structure represented by Formula (II):

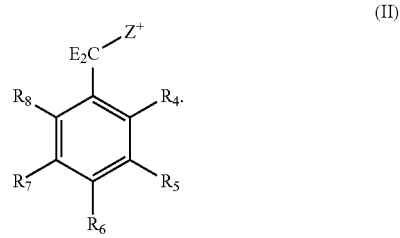

(II)

$Z^+$ is selected from a pyridinium, fluorine-substituted pyridinium, methoxy-substituted pyridinium, quinolinium, or triphenylphosphonium group, and each E is independently hydrogen or deuterium. One of $R_4$-$R_8$ bears a reactivity group that enables the molecular tag to be attached covalently to an analyte, and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof. $Q^+$-A contains at least one O, N or S atom, which is separated from the C atom of the $CE_2Z$ substituent by four or five single or double bonds. The O, N or S atom is part of the $R_4$ group.

Yet another aspect of the invention is a molecular tag having the structure of Formula (I) or Formula (II) as described above.

Another aspect of the invention is another method for detecting an analyte A using a multi-stage mass spectrometer having at least first and second stages. The method includes the steps of: (a) contacting a sample containing the analyte with a molecular tag $Q^+$, whose structure is as defined in Formula (I) above, whereby the analyte is covalently labeled with the molecular tag to produce tagged analyte $Q^+$-A, (b) subjecting $Q^+$-A to volatization into the gas phase and then filtration in the first stage; (c) subjecting $Q^+$-A to cleavage by energetic activation to form a resonance-stabilized first product ion $q^+$-A and a neutral amine, wherein $q^+$ and the neutral amine are both fragments of $Q^+$; (d) filtering $q^+$-A in the second stage; (e) subjecting $q^+$-A to cleavage by energetic activation to form a second product ion $q^+$-A', wherein A' is a fragment of A; (f) filtering $q^+$-A', and (g) detecting $q^+$-A'.

The invention is further summarized by the following list of items.

1. A method for detecting an analyte A using a multi-stage mass spectrometer having at least first and second stages, the method comprising the steps of:
    (a) contacting a sample containing the analyte with a molecular tag $Q^+$, whereby the analyte is covalently labeled with the molecular tag to produce tagged analyte $Q^+$-A,
    wherein $Q^+$ is represented by Formula (I)

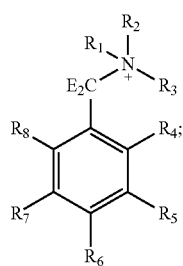

(I)

wherein $R_1$, $R_2$, and $R_3$ are each independently selected from methyl, ethyl, propyl, cyclopropyl, isopropyl, butyl, fluoromethyl, difluoromethyl, trifluoromethyl, fluoroethyl, difluoroethyl, trifluoroethyl, cyanomethyl, cyanoethyl, hydroxyethyl, methoxyethyl, and nitroethyl, and E is hydrogen or deuterium;
   wherein one of $R_4$-$R_8$ bears a reactivity group that enables $Q^+$ to be attached covalently to the analyte to form $Q^+$-A, wherein the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof; wherein each $CE_2COCE_3$, $CE_2CONE_2$, $CE_2NHCOCE_3$, $CE_2OG$, $CE_2SG$, OG and SG is ortho or para to the $CE_2NR_1R_2R_3$ substituent;
   wherein $Q^+$-A comprises at least one O, N or S atom, provided by the analyte, which is separated from the C atom of the $CE_2NR_1R_2R_3$ substituent by three, four or five single or double bonds, and the O, N, or S atom is in a group which is ortho to the $CE_2NR_1R_2R_3$ substituent;
   (b) subjecting $Q^+$-A to volatization into the gas phase and then filtration in the first stage;
   (c) subjecting $Q^+$-A to cleavage by energetic activation to form a resonance-stabilized first product ion $q^+$-A and a neutral amine, wherein $q^+$ and the neutral amine are both fragments of $Q^+$;
   (d) filtering $q^+$-A in the second stage; and
   (e) detecting $q^+$-A.

2. A method for detecting an analyte A using a multi-stage mass spectrometer having at least first and second stages, the method comprising the steps of:
    (a) contacting a sample containing the analyte with a molecular tag $Q^+$, whereby the analyte is covalently labeled with the molecular tag to produce tagged analyte $Q^+$-A,
    wherein $Q^+$ is represented by Formula (I)

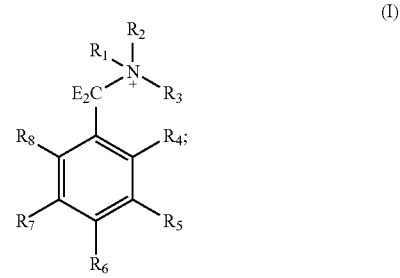

(I)

wherein $R_1$, $R_2$, and $R_3$ are each independently selected from methyl, ethyl, propyl, cyclopropyl, isopropyl, butyl, fluoromethyl, difluoromethyl, trifluoromethyl, fluoroethyl, difluoroethyl, trifluoroethyl, cyanomethyl, cyanoethyl, hydroxyethyl, methoxyethyl, and nitroethyl, and E is hydrogen or deuterium;
   wherein one of $R_4$-$R_8$ bears a reactivity group that enables $Q^+$ to be attached covalently to the analyte to form $Q^+$-A, wherein the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof; wherein each $CE_2COCE_3$, $CE_2CONE_2$, $CE_2NHCOCE_3$, $CE_2OG$, $CE_2SG$, OG and SG is ortho or para to the $CE_2NR_1R_2R_3$ substituent;
   wherein $Q^+$-A comprises at least one O, N or S atom, provided by the analyte, which is separated from the C atom of the $CE_2NR_1R_2R_3$ substituent by three, four or five single or double bonds, and the O, N, or S atom is in a group which is ortho to the $CE_2NR_1R_2R_3$ substituent;
   (b) subjecting $Q^+$-A to volatization into the gas phase and then filtration in the first stage;
   (c) subjecting $Q^+$-A to cleavage by energetic activation to form a resonance-stabilized first product ion $q^+$-A and a neutral amine, wherein $q^+$ and the neutral amine are both fragments of $Q^+$;
   (d) filtering $q^+$-A in the second stage;
   (e) subjecting $q^+$-A to cleavage by energetic activation to form a second product ion $q^+$-A', wherein A' is a fragment of A;
   (f) filtering $q^+$-A', and
   (g) detecting $q^+$-A'.

3. The method of item 1, wherein $Q^+$-A after filtration in the first stage but prior to filtration in the second stage undergoes two cleavages to form $q^+$-A' which is then filtered and detected.

4. The method of any of the preceding items, wherein the reactivity group of $Q^+$ is selected from the group consisting of $CH_2X$, wherein X is Cl, Br, or I; $CH_2OH$, $CH_2SH$; $CH_2I$, $CH_2NH_2$; $CH_2NHNH_2$, $CH_2OSO_2C_6H_4CH_3$, $CH_2OSO_2CF_3$, $CH_2$-(2-oxy-N-methylpyridinium); $C_6H_4NH_2$, $CH_2OC_6H_4NH_2$, $CH_2OCH_2C_6H_4CH_2NH_2$, CHO; $CH_2OC_6H_4SO_2Cl$, $CH_2OCH_2C_6H_4SO_2NHNH_2$, CH$_2$ONH$_2$; CH$_2$OC$_6$H$_4$NO, CH$_2$N$_3$, CH$_2$COCl, COCl, CH$_2$NCOCH$_2$Br, CONHNH$_2$; CH$_2$CHO; CH$_2$CONHNH$_2$, CH$_2$NCS; CH$_2$CO$_2$H, C$_6$H$_4$CO$_2$H, CH$_2$C$_6$H$_4$CO$_2$H, CO$_2$H, CH$_2$OC$_6$H$_4$CO$_2$H, and CH$_2$OCH$_2$CO$_2$H.

5. The method of item 4, wherein the reactivity group of Q$^+$ is CH$_2$Br.

6. The method of any of the preceding items, wherein Q$^+$ is α-triethylammonium-α'-bromo-ortho-xylene (TEBX).

7. The method of any of items 1-5, wherein Q$^+$ is selected from the following compounds:

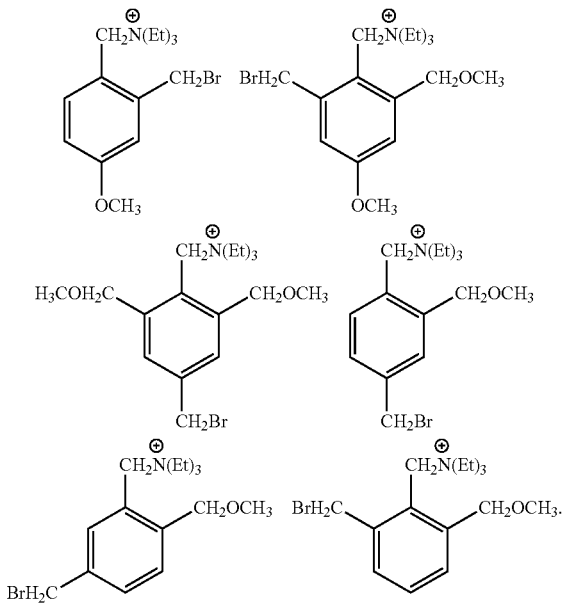

8. The method of any of the preceding items, wherein the total number of said N, O, or S atoms is 2.

9. The method of any of the preceding items, wherein the total number of said N, O or S atoms is 3.

10. The method of any of items 1-5, wherein R$_5$ or R$_6$ bears said reactivity group and the remainder of R$_4$-R$_8$ are independently selected from H, D, CE$_2$COCE$_3$, CE$_2$CONE$_2$, CE$_2$NHCOCE$_3$, CE$_2$OG, CE$_2$SG, OG, and SG.

11. The method of any of the preceding items, wherein the sample is of environmental or biological origin.

12. A method for detecting an analyte A using a multi-stage mass spectrometer having at least first and second stages, the method comprising the steps of:
(a) contacting a sample containing the analyte with a molecular tag Q$^+$, whereby the analyte is covalently labeled with the molecular tag to produce tagged analyte Q$^+$-A,
wherein Q$^+$ is represented by Formula (II)

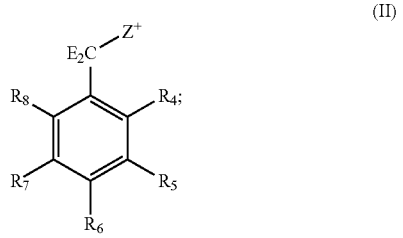

wherein Z$^+$ is selected from pyridinium, fluorine-substituted pyridinium, methoxy-substituted pyridinium, quinolinium, or triphenylphosphonium group, and E is hydrogen or deuterium;
wherein one of R$_4$-R$_8$ bears a reactivity group that enables Q$^+$ to be attached covalently to the analyte to form Q$^+$-A, wherein the remainder of R$_4$-R$_8$ are independently selected from H, D, CE$_2$COCE$_3$, CE$_2$CONE$_2$, CE$_2$NHCOCE$_3$, CE$_2$OG, CE$_2$SG, OG, and SG, wherein G is methyl, ethyl, or propyl bearing H or D atoms, or a combination thereof; wherein each CE$_2$COCE$_3$, CE$_2$CONE$_2$, CE$_2$NHCOCE$_3$, CE$_2$OG, CE$_2$SG, OG and SG is ortho or para to the CE$_2$Z$^+$ substituent;
wherein Q$^+$-A comprises at least one O, N or S atom, provided by the analyte, which is separated from the C atom of the CE$_2$Z$^+$ substituent by three, four or five single or double bonds, and the O, N, or S atom is in a group which is ortho to the CE$_2$Z substituent;
(b) subjecting Q$^+$-A to volatization into the gas phase and then filtration in the first stage;
(c) subjecting Q$^+$-A to cleavage by energetic activation to form a resonance-stabilized first product ion q$^+$-A and a neutral amine, wherein q$^+$ and the neutral amine are both fragments of Q$^+$;
(d) filtering q$^+$-A in the second stage; and
(e) detecting q$^+$-A.

13. A method for detecting an analyte A using a multi-stage mass spectrometer having at least first and second stages, the method comprising the steps of:
(a) contacting a sample containing the analyte with a molecular tag Q$^+$, whereby the analyte is covalently labeled with the molecular tag to produce tagged analyte Q$^+$-A,
wherein Q$^+$ is represented by Formula (II)

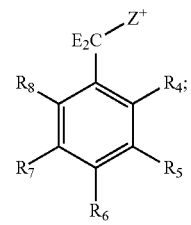

wherein Z$^+$ is selected from pyridinium, fluorine-substituted pyridinium, methoxy-substituted pyridinium, quinolinium, or triphenylphosphonium group, and E is hydrogen or deuterium;
wherein one of R$_4$-R$_8$ bears a reactivity group that enables Q$^+$ to be attached covalently to the analyte to form Q$^+$-A, wherein the remainder of R$_4$-R$_8$ are independently selected from H, D, CE$_2$COCE$_3$, CE$_2$CONE$_2$, CE$_2$NHCOCE$_3$, CE$_2$OG, CE$_2$SG, OG, and SG, wherein G is methyl, ethyl, or propyl bearing H or D atoms, or a combination thereof; wherein each CE$_2$COCE$_3$, CE$_2$CONE$_2$, CE$_2$NHCOCE$_3$, CE$_2$OG, CE$_2$SG, OG and SG is ortho or para to the CE$_2$Z$^+$ substituent;
wherein Q$^+$-A comprises at least one O, N or S atom, provided by the analyte, which is separated from the C atom of the CE$_2$Z$^+$ substituent by three, four or five single or double bonds, and the O, N, or S atom is in a group which is ortho to the CE$_2$Z substituent;

(b) subjecting $Q^+$-A to volatization into the gas phase and then filtration in the first stage;
(c) subjecting $Q^+$-A to cleavage by energetic activation to form a resonance-stabilized first product ion $q^+$-A and a neutral amine, wherein $q^+$ and the neutral amine are both fragments of $Q^+$;
(d) filtering $q^+$-A in the second stage;
(e) subjecting $q^+$-A to cleavage by energetic activation to form a second product ion $q^+$-A', wherein A' is a fragment of A;
(f) filtering $q^+$-A', and
(g) detecting $q^+$-A'.

14. The method of item 12, wherein $Q^+$-A after filtration in the first stage but prior to filtration in the second stage undergoes two cleavages to form $q^+$-A' which is then filtered and detected.

15. The method of any of items 12-14, wherein the reactivity group of $Q^2$ is selected from the group consisting of $CH_2X$, wherein X is Cl, Br, or I; $CH_2OH$; $CH_2SH$; $CH_2I$, $CH_2NH_2$; $CH_2NHNH_2$; $CH_2OSO_2C_6H_4CH_3$, $CH_2OSO_2CF_3$, $CH_2$-(2-oxy-N- methylpyridinium); $C_6H_4NH_2$, $CH_2OC_6H_4NH_2$, $CH_2OCH_2C_6H_4CH_2NH_2$, CHO; $CH_2OC_6H_4SO_2Cl$, $CH_2OCH_2C_6H_4SO_2NHNH_2$, $CH_2ONH_2$; $CH_2OC_6H_4NO$, $CH_2N_3$, $CH_2COCl$, COCl, $CH_2NCOCH_2Br$, $CONHNH_2$; $CH_2CHO$; $CH_2CONHNH_2$, $CH_2NCS$; $CH_2CO_2H$, $C_6H_4CO_2H$, $CH_2C_6H_4CO_2H$, $CO_2H$, $CH_2OC_6H_4CO_2H$, and $CH_2OCH_2CO_2H$.

16. The method of item 15, wherein the reactivity group of $Q^+$ is $CH_2Br$.

17. The method of any of items 12-16, wherein the total number of said N, O, or S atoms is 2.

18. The method of any of items 12-17, wherein the total number of said N, O or S atoms is 3.

19. The method of any of items 12-18, wherein $R_5$ or $R_6$ bears said reactivity group and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG.

20. The method of any of items 12-19, wherein the sample is of environmental or biological origin.

21. A molecular tag for identification of an analyte by multi-stage mass spectrometry, the molecular tag having a structure according to Formula (I)

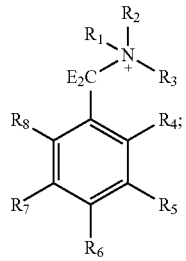

wherein $R_1$, $R_2$, and $R_3$ are each independently selected from methyl, ethyl, propyl, cyclopropyl, isopropyl, butyl, fluoromethyl, difluoromethyl, trifluoromethyl, fluoroethyl, difluoroethyl, trifluoroethyl, cyanomethyl, cyanoethyl, hydroxyethyl, methoxyethyl, and nitroethyl, and E is hydrogen or deuterium;
wherein one of $R_4$-$R_8$ bears a reactivity group that enables the molecular tag to be attached covalently to an analyte; and
wherein the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof; wherein each $CE_2COCE_3$, $CE_2CONE_2$, $CE_2NHCOCE_3$, $CE_2OG$, $CE_2SG$, OG and SG is ortho or para to the $CE_2NR_1R_2R_3$ substituent.

22. The molecular tag of item 21, wherein the reactivity group is selected from the group consisting of $CH_2X$, wherein X is Cl, Br, or I; $CH_2OH$; $CH_2SH$; $CH_2I$, $CH_2NH_2$; $CH_2NHNH_2$; $CH_2OSO_2C_6H_4CH_3$, $CH_2OSO_2CF_3$, $CH_2$-(2-oxy-N-methylpyridinium), $C_6H_4NH_2$, $CH_2OC_6H_4NH_2$, $CH_2OCH_2C_6H_4CH_2NH_2$, CHO; $CH_2OC_6H_4SO_2Cl$, $CH_2OCH_2C_6H_4SO_2NHNH_2$, $CH_2ONH_2$; $CH_2OC_6H_4NO$, $CH_2N_3$, $CH_2COCl$, COCl, $CH_2NCOCH_2Br$, $CONHNH_2$; $CH_2CHO$; $CH_2CONHNH_2$, $CH_2NCS$; $CH_2CO_2H$, $C_6H_4CO_2H$, $CH_2C_6H_4CO_2H$, $CO_2H$, $CH_2OC_6H_4CO_2H$, and $CH_2OCH_2CO_2H$.

23. The molecular tag of item 22, wherein the reactivity group is $CH_2Br$.

24. The molecular tag of any of items 21-23 which is α-triethylammonium-α'-bromo-ortho-xylene (TEBX).

25. The molecular tag of any of items 21-23, wherein $R_5$ or $R_6$ bears said reactivity group and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG.

26. The molecular tag of any of items 21-23 which is selected from the following compounds:

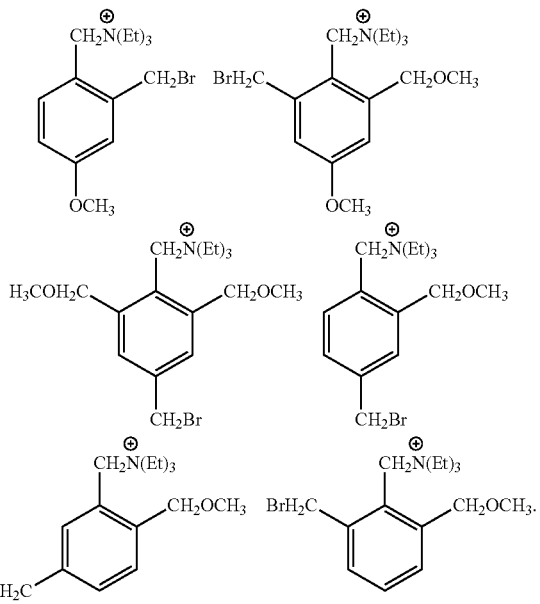

27. A molecular tag for identification of an analyte by multi-stage mass spectrometry, the molecular tag having a structure according to Formula (II):

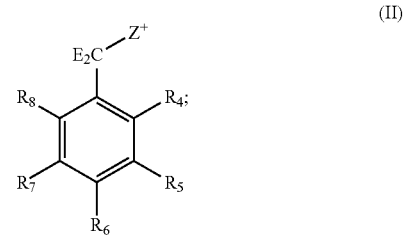

wherein $Z^+$ is selected from pyridinium, fluorine-substituted pyridinium, methoxy-substituted pyridinium, quinolinium, or triphenylphosphonium group, and E is hydrogen or deuterium;

wherein one of $R_4$-$R_8$ bears a reactivity group that enables the molecular tag to be attached covalently to an analyte; and wherein the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof; wherein each $CE_2COCE_3$, $CE_2CONE_2$, $CE_2NHCOCE_3$, $CE_2OG$, $CE_2SG$, OG and SG is ortho or para to the $CE_2Z^+$ substituent.

28. The molecular tag of item 27, wherein the reactivity group is selected from the group consisting of $CH_2X$, wherein X is Cl, Br, or I; $CH_2OH$; $CH_2SH$; $CH_2I$, $CH_2NH_2$; $CH_2NHNH_2$; $CH_2OSO_2C_6H_4CH_3$, $CH_2OSO_2CF_3$, $CH_2$-(2-oxy-N-methylpyridinium), $C_6H_4NH_2$, $CH_2OC_6H_4NH_2$, $CH_2OCH_2C_6H_4CH_2NH_2$, CHO; $CH_2OC_6H_4SO_2Cl$, $CH_2OCH_2C_6H_4SO_2NHNH_2$, $CH_2ONH_2$; $CH_2OC_6H_4NO$, $CH_2N_3$, $CH_2COCl$, COCl, $CH_2NCOCH_2Br$, $CONHNH_2$; $CH_2CHO$; $CH_2CONHNH_2$, $CH_2NCS$; $CH_2CO_2H$, $C_6H_4CO_2H$, $CH_2C_6H_4CO_2H$, $CO_2H$, $CH_2OC_6H_4CO_2H$, and $CH_2OCH_2CO_2H$.

29. The molecular tag of item 28, wherein the reactivity group is $CH_2Br$.

30. The molecular tag of any of items 27-29, wherein $R_5$ or $R_6$ bears said reactivity group and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG.

BRIEF DESCRIPTION OF THE DRAWINGS

FIG. 5A shows detection of the first product ion. FIG. 5B shows detection of the second product ion in a pseudo MS3 mode. FIG. 5C shows detection of the second product ion in a true MS3 mode.

FIG. 6A shows the MS detection, and FIG. 6B shows the fragmentation sites of TEBX-acyclovir and molecular masses of the fragments.

FIGS. 8A-8B show the detection of a series of phenols using TEBX as mass tag. The m/z ratios of the phenol compounds are listed in FIG. 8A, and the separation and detection of the TEBX-phenol compound precursor ions are shown in FIG. 8B.

DETAILED DESCRIPTION OF THE INVENTION

Figure 1:
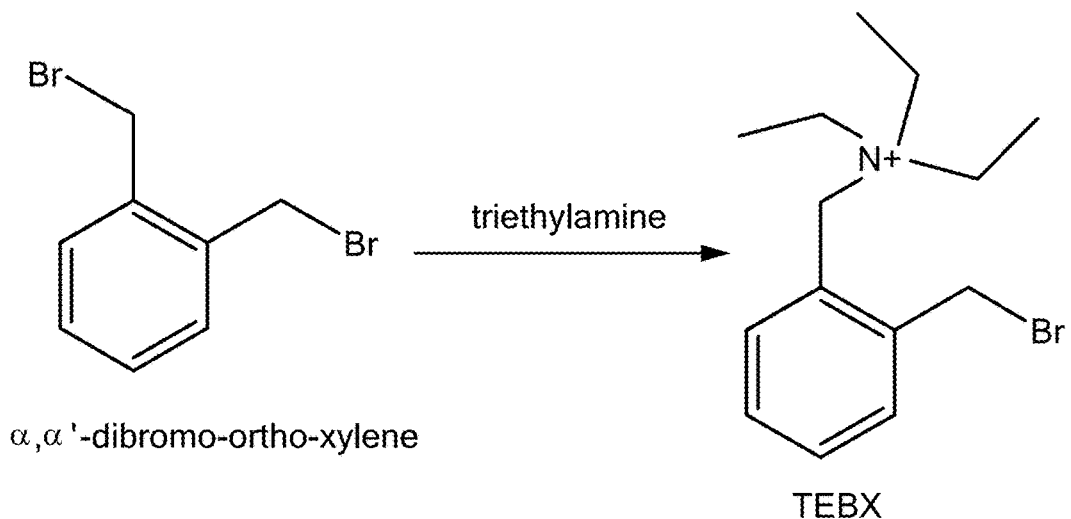
FIG. 1 shows a reaction scheme for the synthesis of TEBX, an MS3 tag for both true MS3 and pseudo MS3 detection of analytes.

The present invention provides methods and compounds that improve the use of mass tags in mass spectrometry and make possible the detection of analytes with extreme sensitivity, down to the attomole level.

According to the invention, the following sequence of steps can result in specific, extremely ultrasensitive detection (amol level) of an analyte molecule of interest: (1) covalently tag the analyte molecule on a heteroatom with a mass tag having a quaternary amino group, such as α-triethylammonium-α'-bromo-ortho-xylene (TEBX), or an analog thereof, yielding a tagged analyte (e.g., TEBX-analyte); (2) optionally subject the tagged analyte to one or more cleanup steps such as chromatography; and (3) introduce the tagged analyte into a mass spectrometer that provides at least two stages of mass spectrometry, where the heteroatom promotes fragmentation of the quaternary amino group to yield a benzylic cation as a first product ion. The first product ion, in turn, can undergo further cleavage to efficiently form an analyte-characteristic, second product ion of the analyte. The second product cation is a fragment of the first product ion, and includes a portion of the analyte and may also include part of the tag.

The extreme ultrasensitivity arises from the properties of the tagged analyte molecule to both volatilize efficiently with retention of charge in the ion source of the mass spectrometer, and then to efficiently follow a fragmentation pathway to an analyte-characteristic second product ion via anchimeric assisted formation of the first product ion and further fragmentation to the second product ion. The second product ion can be detected either in a two-stage mass spectrometer, providing pseudo three stage mass spectrometry (pseudo-MS3), or in a three stage mass spectrometer (true MS3).

The invention utilizes a new class of mass tags referred to herein as "anchimeric mass tags" (AMTs). When reacted with a suitable analyte molecule, such tags form a cationic precursor ion in the first stage of a multistage mass spectrometer. AMTs utilize anchimeric assistance (neighboring group participation) to help eject a neutral fragment when the cationic precursor ion is subjected to collision-induced dissociation (CID) in the gas stream of the mass spectrometer. This promotes the formation of a first product carbocation, the detection of which is more specific than detection of the precursor ion, since much of the general background noise (background ions from sample and reagent impurities) will lack this fragmentation pathway, or lack a fragmentation pathway that can yield an isobaric ion relative to the first product ion. More importantly, the enhanced formation of a first product carbocation enables a higher yield of a second product carbocation, which gives an additional boost in specificity and thereby sensitivity, by decreasing the noise much more than the signal during detection. Extreme ultrasensitivity can be achieved for a favorable analyte (an analyte for which the successive yields of the precursor ion (from the ion source), first product ion (from CID on the precursor ion), and second product ion (from CID on the first product ion) are all high.

In a true MS3 analysis, measurement of a precursor ion is considered as MS1; measurement of the first product ion after isolation (filtering) and CID of the precursor ion is considered as MS2; and measurement of the second product ion (after subsequent isolation and CID of the first product ion) is considered as MS3. In a related pseudo-MS3 analysis, the second product ion is formed from the precursor ion in a single CID step. A pseudo MS3 analysis can also provide extreme ultrasensitivity and specificity.

The anchimeric atom or group of the AMT-analyte conjugate (AMT-labeled analyte, or AMT-analyte), acts by stabilizing the first product ion which in turn facilitates its formation from the precursor ion. For example, the departure of a tertiary amine or protonated secondary amine as a neutral moiety from connection to a carbon atom in the precursor ion, yielding a carbocation, can be anchimerically assisted by a lone pair of electrons from a nearby oxygen, nitrogen, or sulfur atom, or by the pi electrons of a group such as an alkene, azo, alkyne, or phenyl moiety. It is preferred that the carbocation inherently have enhanced stability by resonance delocalization of the charge, e.g. a benzylic carbocation, an analogous naphthylmethyl carbocation, or allylic carbocation. The anchimeric atom or group can be built inherently into the AMT prior to coupling of the AMT to an analyte, or be created when the analyte is labeled by the AMT. For example, reaction of an AMT, in which a benzylbromide is the reactive group, with a hydroxylic or sulfhydryl analyte, forming a benzyloxy or benzylthio linkage, respectively, thereby installs an anchimeric atom in the AMT-labeled analyte.

The methods of the invention can be practiced with TEBX or a number of analogs of TEBX, such as compounds in which the reactive $CH_2Br$ group is replaced with a reactive group selected from or similar to the following: $CH_2OH$, $CH_2SH$, $CH_2I$, $CH_2NH_2$, $CH_2NHNH_2$, $CH_2OSO_2C_6H_4CH_3$, $CH_2OSO_2CF_3$, $CH_2$-(2-oxy-N-methylpyridinium), $C_6H_4NH_2$, $CH_2OCH_2C_6H_4CH_2NH_2$, CHO, $CH_2OC_6H_4SO_2Cl$, $CH_2OCH_2C_6H_4SO_2NHNH_2$, $CH_2ONH_2$, $CH_2OC_6H_4NO$, $CH_2N_3$, $CH_2COCl$, COCl, $CH_2NCOCH_2Br$, $CONHNH_2$, $CH_2CHO$, $CH_2CONHNH_2$, $CH_2NCS$, $CH_2OC_6H_4NH_2$, $CH_2CO_2H$, $C_6H_4CO_2H$, $CH_2C_6H_4CO_2H$, $CO_2H$, $CH_2OC_6H_4CO_2H$, and $CH_2OCH_2CO_2H$.

When the reactive moiety of a reactive group is a carboxyl, activation of this carboxyl is required. This can be done by converting it to a carbonylimidazole with carbonyldiimidazole; to an N-hydroxysuccinimide ester with a carbodiimide reagent such as dicyclohexylcarbodiimide or N-(2-dimethylaminopropyl)-N'-ethylcarbodiimide and N-hydroxysuccinimide; by activating it with 7-azabenzotriazol-1-yloxy) tripyrrolidino-phosphonium hexafluorophosphate (PyAOP); by converting it to a N-hydroxybenzotriazole ester with N-hydroxybenzotriazole and a carbodiimide; to a mixed anhydride as with 2-methyl-6-nitrobenzoic anhydride and 4-dimethylaminopyridine; by activating it with 4-(4,6-dimethoxy-1,3,5-triazin-2-yl)-4-methylmorpholinium chloride; by activating it with 2-chloro-1-methylpyridinium iodide; or by activating it with a carbodiimide reagent in the presence of 4-di methylamino)pyridine.

Other reactive groups that can be used in AMTs are 2,3-naphthalenediamine, 1,2,4-triazoline-3,5-dione, 2-benzyloxy-1-methylpyridinium triflate, and maleimide.

The invention further can be practiced with analogs of TEBX such as corresponding compounds in which the reactive $CH_2Br$ group is replaced with a $CH_2OR$, $CH_2NHR$ or $CH_2SR$ group where R is $CH_2CH_2CO_2H$, $CH_2CH_2CONHNH_2$, $CH_2CH_2NHNH_2$, $CH_2CH_2ONH_2$, $CH_2CH_2COCH_2Br$, $CH_2CH_2COCH_2I$, $CH_2CH_2N=C=O$, and $CH_2CH_2N=C=S$. This invention further can be practiced with naphthyl analogs of TEBX in which a $CH_2Br$ or other reactive group, as defined above, is located adjacent to a triethylaminomethylene group; for example these two groups in combination can occupy the 1,2 or 2,3 or 3,4 or 1,8 positions of a naphthalene moiety. The invention can be practiced similarly with other aryl groups housing nearby reactive and anchimeric groups.

The invention further can be practiced with analogs of TEBX such as corresponding compounds in which the $CH_2Br$, or other reactive group as indicated above, is at the 1-position on a benzene ring, the triethylaminomethyl group is at the 3 position, and an anchimeric assistance group selected from the above or the following is located at the 4 position: $CH_2OCH_3$, $CH_2SCH_3$, $CH_2NHCH_3$, $CH_2CONH_2$, $CH_2NHCOCH_3$, $CH_2=CH_2$, $CH_2C=CH_2$, $CH_2N=NCH_3$, $NO_2$, $C_6H_5$, and $CH_2C_6H_5$.

The invention further can be practiced with analogs of TEBX such as corresponding compounds in which the $CH_2Br$, or other reactive group as indicated above, is at the 1-position on a benzene ring, the triethylaminomethyl group is at the 4 position, and an anchimeric assistance group is selected from those listed above or the following and is located at the 3 position: $CH_2OCH_2$, $CH_2SCH_3$, $CH_2NHCH_3$, $CH_2CONH_2$, $CH_2NHCOCH_3$, $CH_2COCH_3$, $CH_2=CH_2$, $CH_2C=CH_2$, $CH_2N=NCH_3$, $NO_2$, $C_6H_5$, and $CH_2C_6H_5$.

This invention further can be practiced with tri-substituted naphthalene compounds, where the $CH_2Br$, or other reactive group as indicated above, is located at a given position and the trimethylaminomethyl group and anchimeric assistance group (selected from the groups defined above for tri-substituted benzenes) are located adjacent to each other but without either one being adjacent to the reactive group. For example, the positions of the reactive group, triethylaminomethyl group and the anchimeric assistance group can be located, respectively, at the 1, 3 and 4 positions; at 1,5,6; at 2,5,6; at 3,5,6; at 4,5,6; at 1,6,7; at 2,6,7; at 3,6,7; at 4,6,7; at 2,7,8; at 3,7,8; at 3,1,8; at 4,1,8; and at 4,7,8, as long as there is a N, O, or S atom which is separated by 4 or 5 bonds from the ring-attached C atom of the triethylaminomethyl group, where this N, O, or S atom is part of a group which is adjacent to the triethylaminomethyl group. Further, analogs of the trisubstituted naphthalene compounds can be used in which the positions of the triethylaminomethyl and anchimeric assistance group are exchanged.

In place of an anchimeric group, a group that promotes fragmentation of the precursor ion to yield a benzylic carbocation or naphthymethyl carbocation by a steric effect also can be employed. Steric groups for this purpose can be selected from the following and similar groups: t-butyl, isopropyl, cyclopropyl, phenyl, benzyl, adamantyl, iodo, bromo, trifluoromethyl, and dimethylphenyl. Some of these groups can act through a combination of anchimeric and steric effects. Heteroaromatic groups such as pyridine (e.g., a 2-pyridyl group) can provide steric or anchimeric assistance for the facile formation of a first product cation.

For both benzene and naphthalene core ring structures, the trimethylaminomethyl group can be sandwiched between adjacent reactivity and anchimeric or steric assistance groups. For example, the following positions of reactivity, triethylaminoethyl, and anchimeric/steric groups can be used in benzene or naphthalene core rings: 1,2,3, respectively; or 7,8,1 in naphthalene, respectively.

The invention can be practiced with analogs of the above compounds in which the triethylaminomethyl group is replaced with: (1) a trialkylylaminomethyl group, where alkyl is methylpropyl, cyclopropyl, trifluoromethyl, or a mixture selected from methyl, ethyl, propyl, cyclopropyl and trifluoromethyl groups; (2) a dialkylaminoethyl group where alkyl is methyl, ethyl, propyl, cyclopropyl, trifluoroethyl or a mixture of these groups; (3) any of these groups or mixtures of these groups where one or more hydrogen atoms are replaced with a deuterium atom; (4) a pyridinium group or a quinolinium group.

The invention can be practiced with analogs of the above AMT tags in which the phenyl or naphthyl group is further substituted with one or more atoms or groups selected from deuterium, alkoxy, fluoro, alkyl, fluoroalkyl, aryl, hydroxylalkyl, alkenyl, alkynyl, alkylamindo, bromo, cyano, and nitro.

Methods of the invention can be employed to detect and/or quantify analytes in samples of environmental or biological origin. One example of a class of analytes needing higher detection sensitivity by MS is the human DNA adductome, which includes a list of toxic and carcinogenic chemicals that become covalently stuck on a person's DNA (termed "DNA Adducts"). Discovery analysis is needed to measure the human DNA adductome since it is unique for each person. While DNA adductomes have been partly measured, or measured with partial specificity, in various kinds of biological samples (especially those with a known exposure), there has been no good test for the human DNA adductome previously. This is because MS has not been able to deliver sufficient sensitivity and specificity in a discovery mode for broad detection of known and unknown DNA adducts in human samples.

EXAMPLES

Example 1. Materials and Instrumentation

α,α'-Dibromo-ortho-xylene, α,α'-dibromo-meta-xylene, α,α'-dibromo-para-xylene, triethylamine, α-cyano-4-hydroxycinnamic acid (CCA), thymidine, trifluoroacetic acid (TFA), 17β-estradiol (E2), and acetonitrile (ACN) were from Sigma (St. Louis, Mo.). Microcentrifuge tubes, pipette tips, and HPLC grade acetonitrile (ACN) were from Fisher Scientific (Pittsburgh, Pa.). All materials were used as received.

The MALDI-TOF/TOF-MS instrument was a model 5800 from AB-SCIEX. The LTQ-MS instrument was an LTQ Velos Pro from Thermo Fisher. HPLC for detection of TEBX-thymidine by HPLC-LTQ-MS was as follows. System: Thermo Scientific Ultimate 3000 RSLC; column: 2.1× 50 mm, 1.9 µm Hypersil Gold C18 (Thermos Scientific); column temp: 35° C.; sample tray temp: 10° 0; mobile phase: [A] $H_2O$ with 0.1% formic acid, [B] ACN with 0.1% formic acid; gradient: 10-90% B in 2 min, hold for 0.5 min, re-equilibrate for 0.5 min; flow rate: 0.5 mL/min; injection volume: 5 µL. Cap-LC for detection of TEBX-analyte by Cap-LC-MALDI-TOF/TOF was performed using a Dionex Ultimate system with a column of 0.3×150 mm, 2 µm Acitem PepMed C18 (Thermal Scientific).

Example 2. Synthesis of α-Triethylammonium-α'-Bromo-Ortho-Xylene (TEBX) and Meta/Para Analogs of TEBX TEBX was synthesized according to the reaction scheme shown in FIG. 1. 0.2 g of α,α'-dibromo-ortho-xylene was dissolved in 2 mL CAN. 1.15 molar equivalents of triethylamine were added, and the mixture was kept for 6 h at RT, and then stored at −20° C. overnight. White crystals were formed, which were washed twice with one mL of ice cold acetonitrile using centrifugation. After evaporation of the acetonitrile, 0.217 g of product (TEBX, 79% yield) was obtained as white crystals. Similarly α,α'-dibromo-meta-xylene and α,α'-dibromo-para-xylene were each reacted separately with triethylamine to give meta (mTEBX) and para (pTEBX) analogs, respectively, of TEBX.

Example 3. Synthesis of 2-Triethylaminomethyl-3-Bromomethyl Naphthalene

2-Triethylaminomethyl-3-bromomethyl naphthalene is prepared by reacting bromine with 2,3-dimethylnaphthalene, yielding 2,3-bis[bromomethyl] naphthalene, followed by reaction with triethylamine in the same way that α,α'-dibromo-ortho-xylene was reacted with triethylamine in Example 1.

Example 4. Synthesis of α-Triethylammonium-α'-Iodo-Ortho-Xylene

α-Triethylammonium-α'-iodo-ortho-xylene is obtained by reacting TEBX with sodium iodide in acetonitrile/water.

Example 5. Synthesis of α-Triethylammonium-α'-Carboxymethyloxy-Ortho-Xylene-NHS Ester TEBX is reacted with sodium hydroxide in water, yielding α-triethylammonium α'-hydroxymethyl-ortho-xylene, that in turn was reacted sequentially with iodoacetic acid followed by N-hydroxysuccinimide in the presence of a water soluble carbodiimide to give the product.

Example 6. Analyte Tagging with TEBX and Detection

Figure 2:
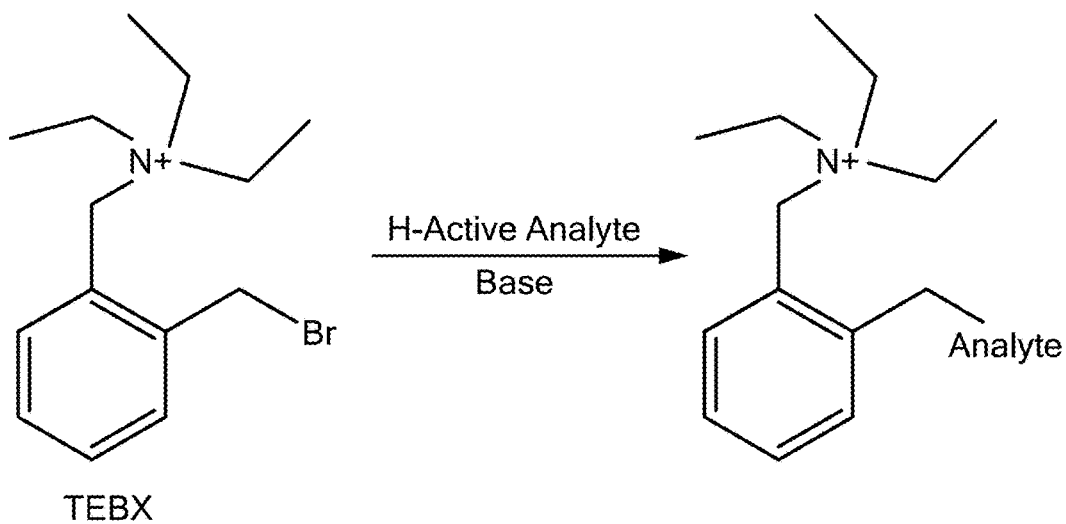
FIG. 2 shows a reaction scheme for labeling an analyte having an active hydrogen with TEBX.

Estradiol, acyclovir, phenolic compounds, and deuterated cytosine as analytes were tagged with TEBX followed by detection by direct MALDI MS as follows. Tagging of the analyte proceeded according to the scheme shown in FIG. 2. TEBX was dissolved in 50% CAN and mixed with the sample, which had been dissolved in CAN. Then, $Et_3N$ was added so that the final concentration of TEBX was 10 mg/mL and of $Et_3N$ was 10 µL/mL. The reaction was allowed to proceed for 2 h at 45° C. The reaction mixture was then mixed 1:9 with CCA matrix, and MALDI-TOF/TOF-MS was performed.

Alternatively, 6 µL of TEBX solution (TEBX at 1 mg/mL in 50% ACN and $Et_3N$ at 10 µL/mL in ACN) was added to a dried sample vial containing the analyte, and the reaction was run for 16 h at 38° C. Subsequently, Cap-LC/MALDI-TOF/TOF was performed.

Figure 3A:
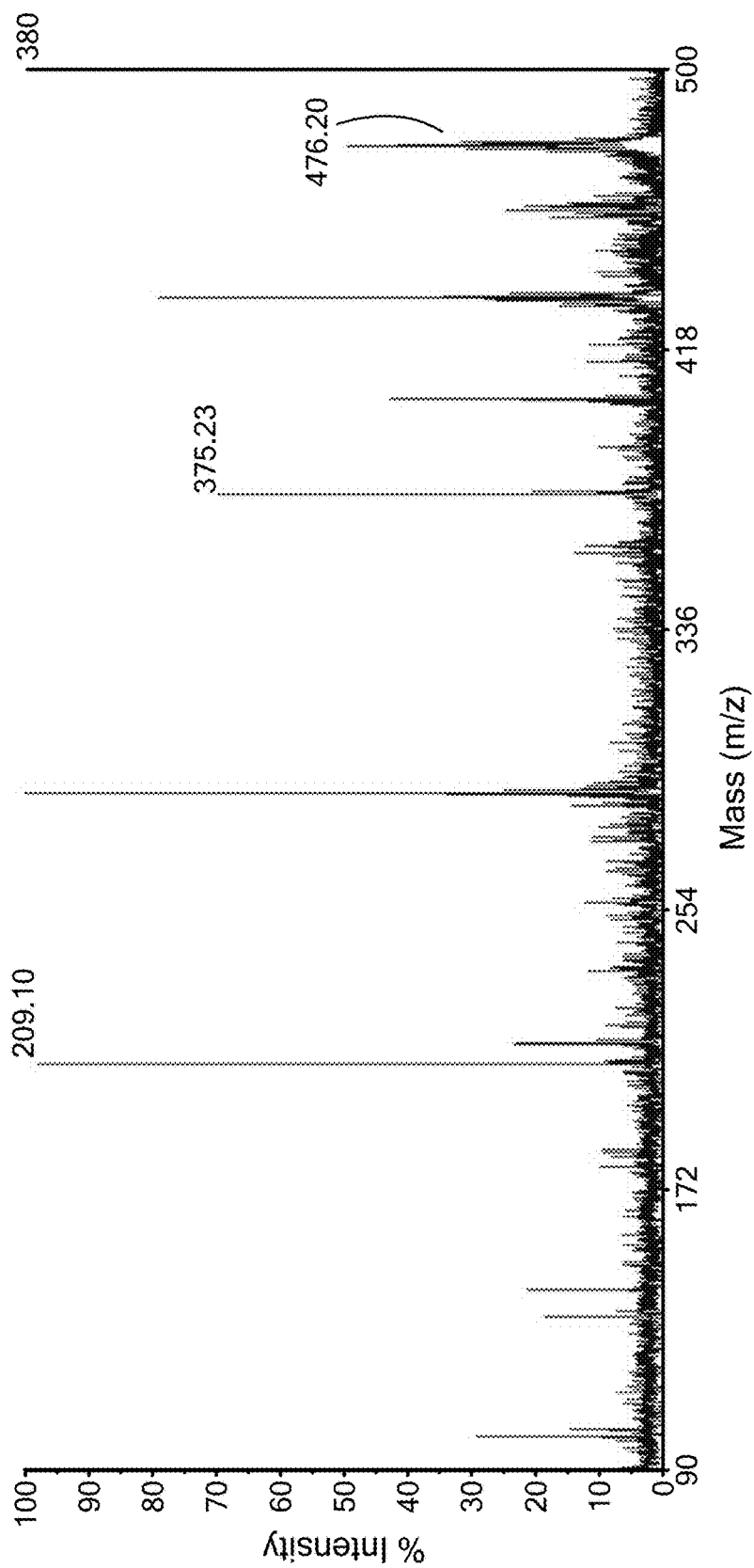
FIGS. 3A and 3B show the detection of 30 amol of TEBX-estradiol by MALDI-TOF/TOF-MS operated in a pseudo-MS3 mode. The MS result is shown in FIG. 3A, and the fragmentation sites and molecular masses of the fragments are shown in FIG. 3B.
Figure 3B:
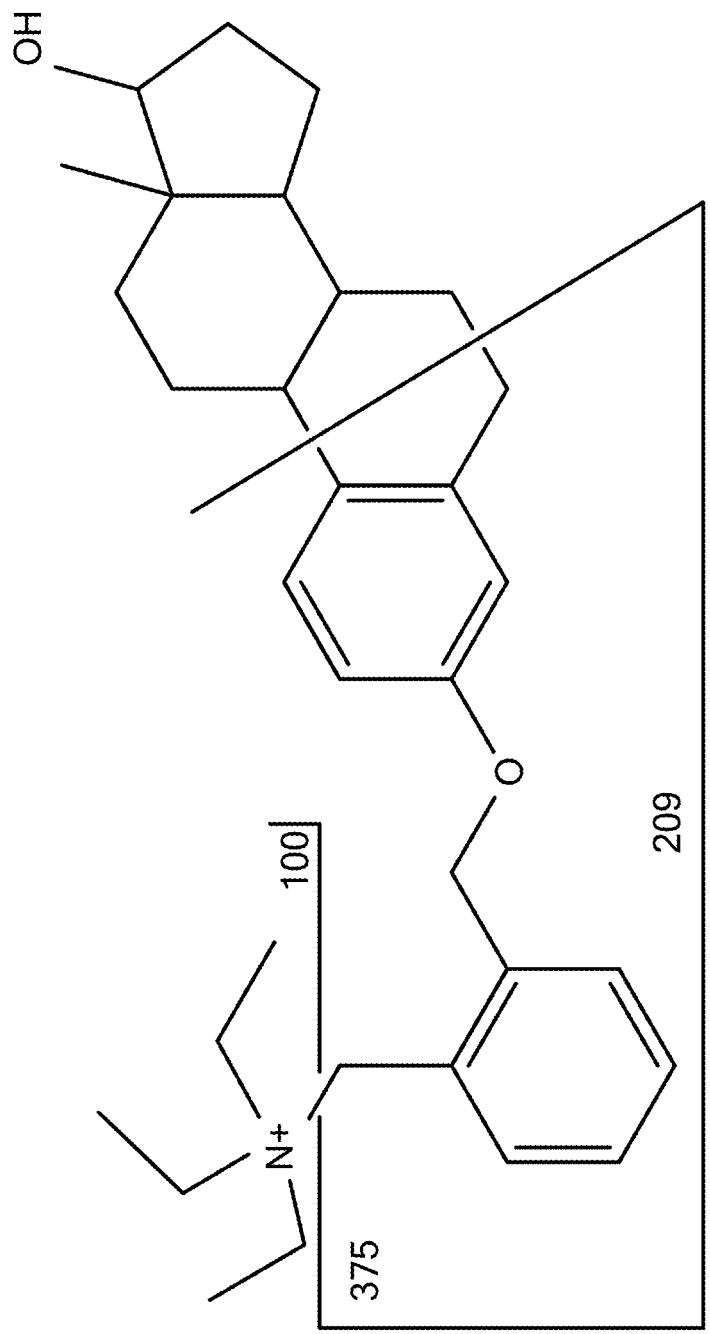
Figure 6A:
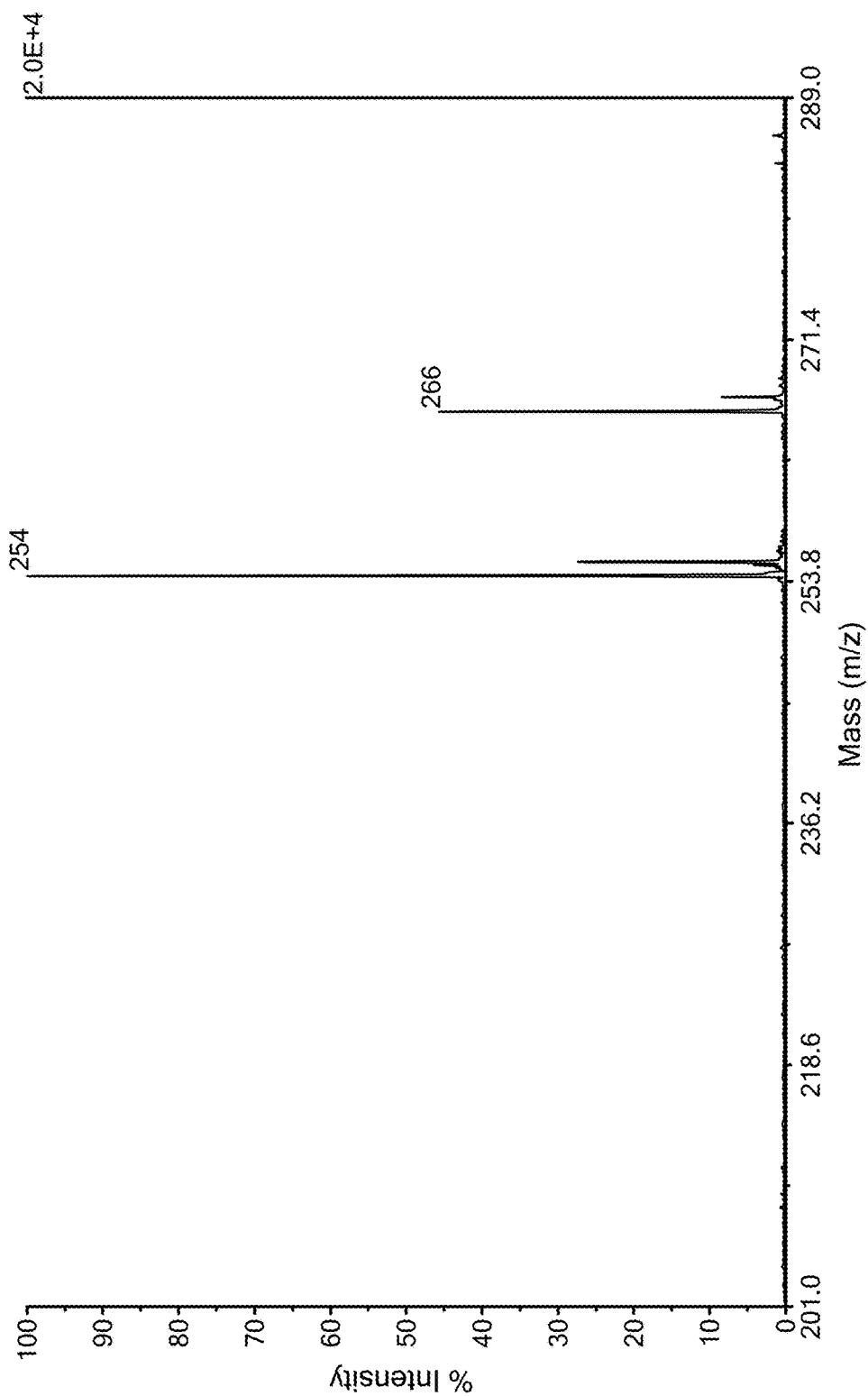
FIGS. 6A-6B show the specific detection of TEBX-acyclovir in a pseudo MS3 mode.
Figure 6B:
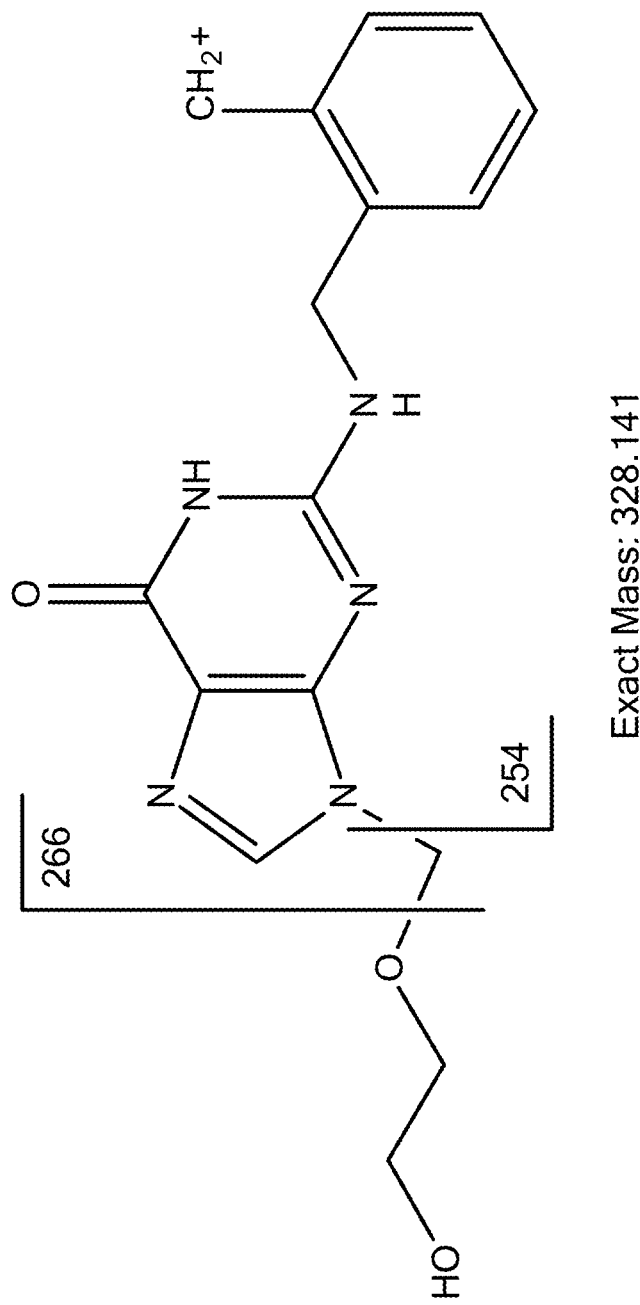
Figure 7:
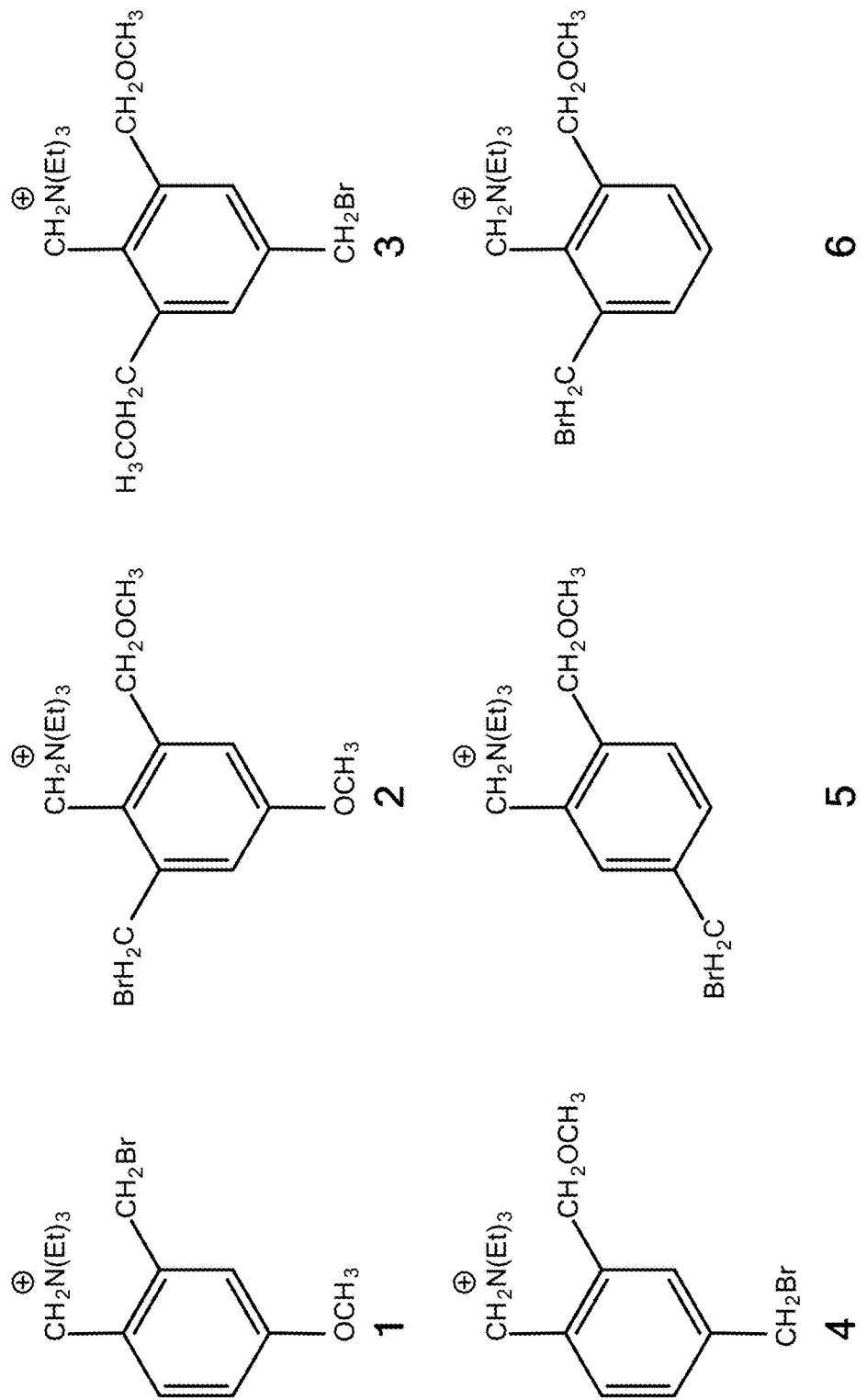
FIG. 7 shows some analogs of TEBX suitable for use as anchimeric mass tags.
Figure 9:
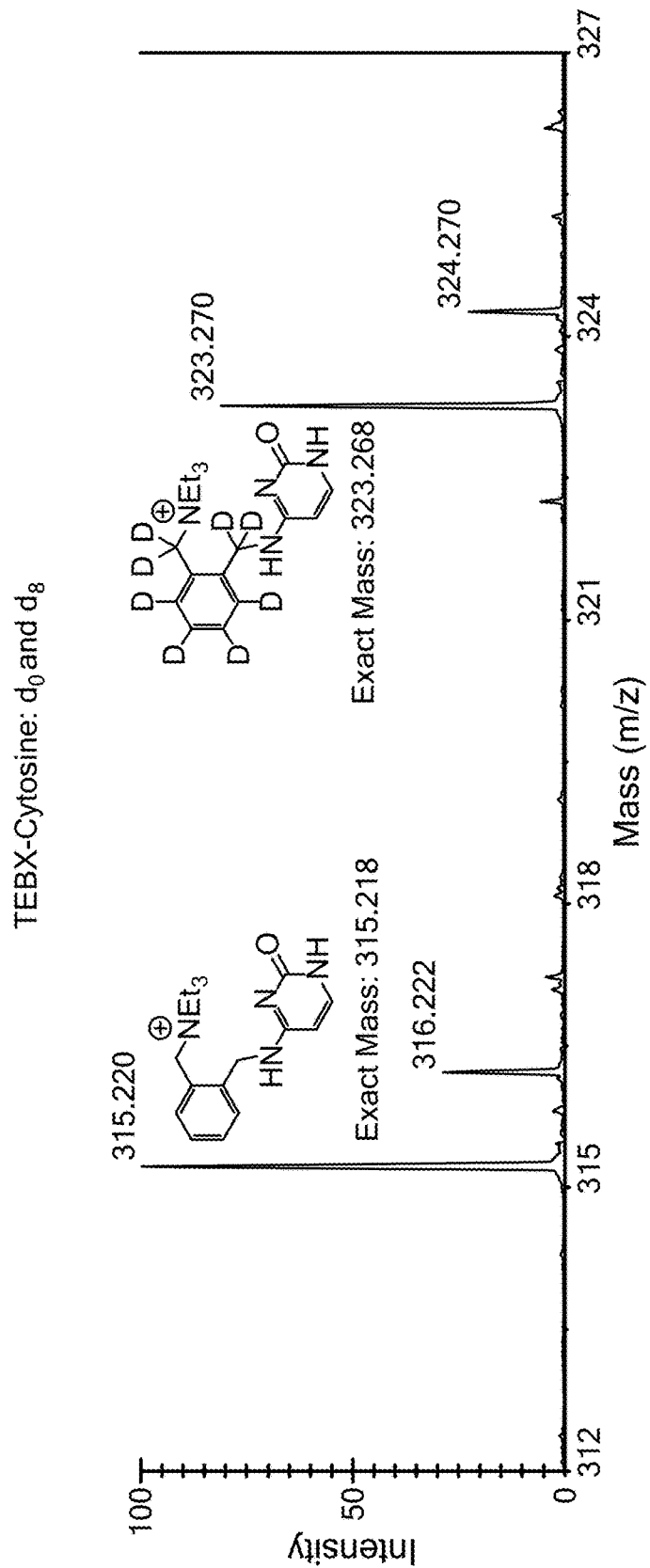
FIG. 9 shows the detection of cytosine and deuterated cytosine using TEBX as a mass tag.

The detection results are shown in FIGS. 3A, 6A, 8A, and 9, while the fragmentation sites and fragment molecular masses are shown in FIGS. 3B, 6B, and 8B.

Example 8. Detection of 160 Amol of Thymidine

Thymidine as analyte was detected via TEBX-labeling followed by HPLC/HPLC/MALDI-TOF/TOF-MS. Six µL of TEBX solution (TEBX at 1 mg/mL in 50% ACN and $Et_3N$ at 10 µL/mL in ACN) was added to a dried sample vial containing 160 amol of thymidine, and the vial was kept for 16 h at 38° C. The solution was dried in a Speed Vac, redissolved in 5 µL of 0.1% TFA, 2% ACN, and injected into a Micro-HPLC system (Agilent 1100, Dionex PepMap 100 C18 column, 1×250 mm, 5 µm). The column was run at a flow rate of 50 µL/min using a mobile phase of 12% ACN with 0.1% TFA for 4 min, followed by a gradient of 12-90%

Figure 4A:
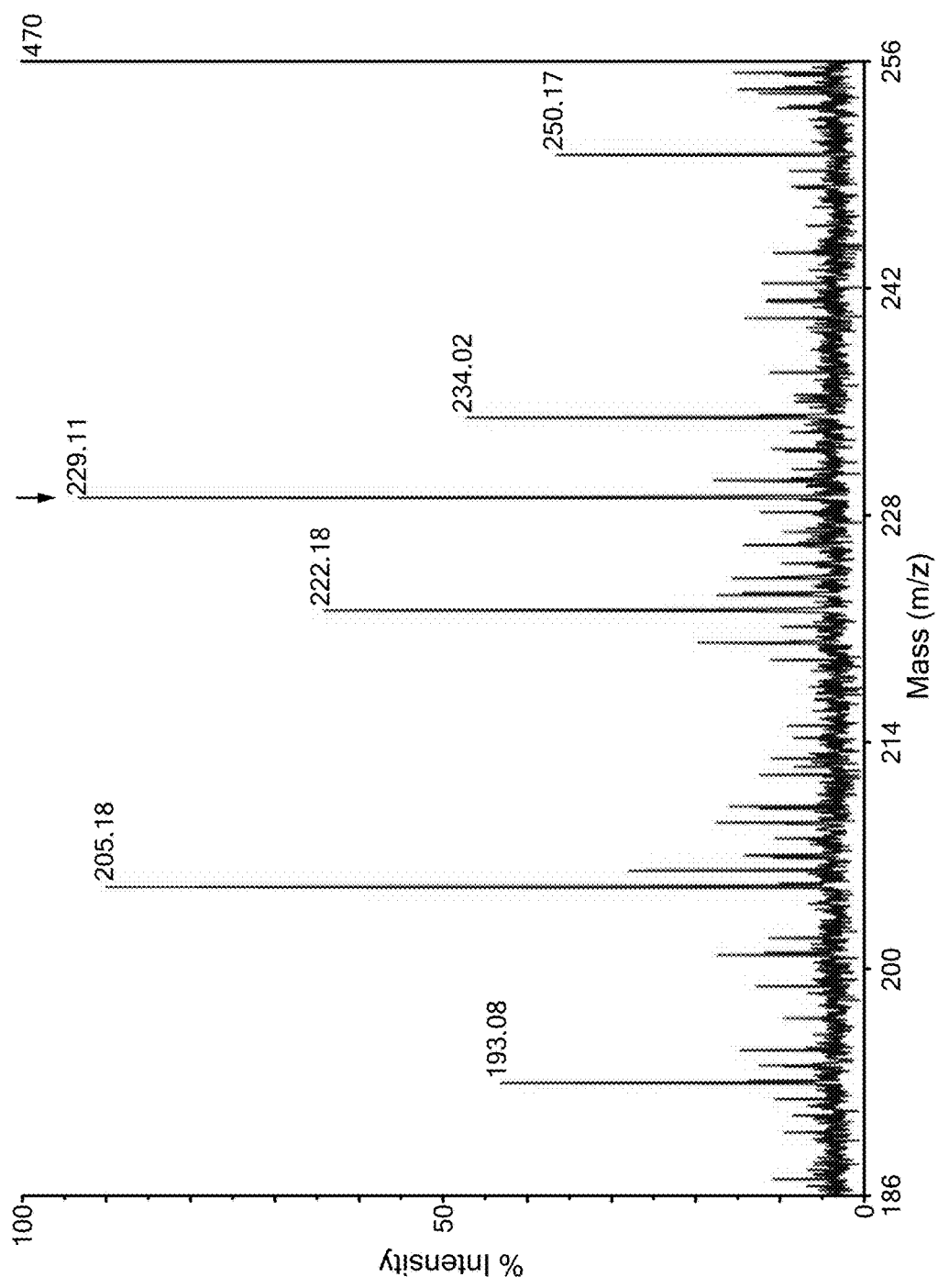
FIGS. 4A and 4B show detection of 160 amol of thymidine by TEBX labeling/HPLC/HPLC/MALDI-TOF/TOF-MS in a pseudo-MS3 mode.
Figure 4B:
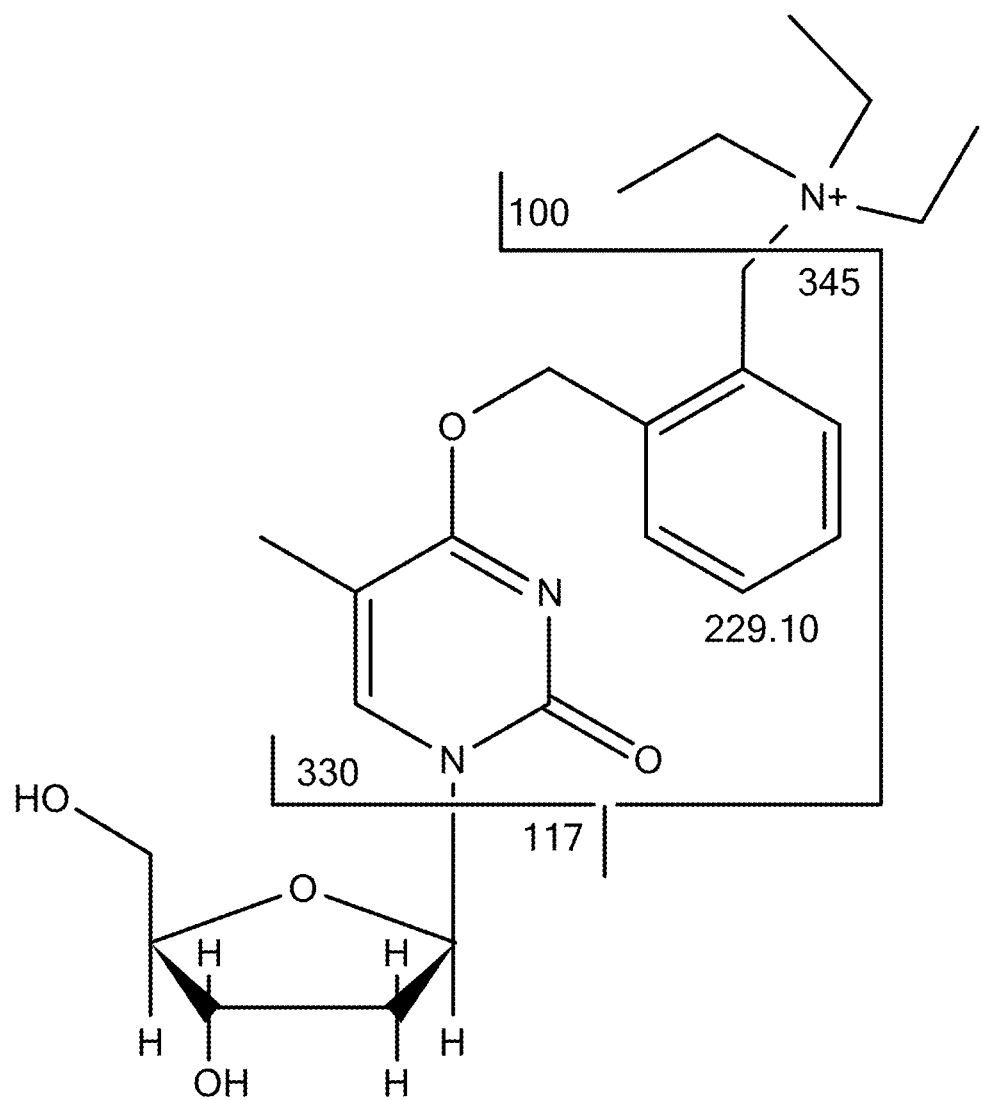
Figure 5A:
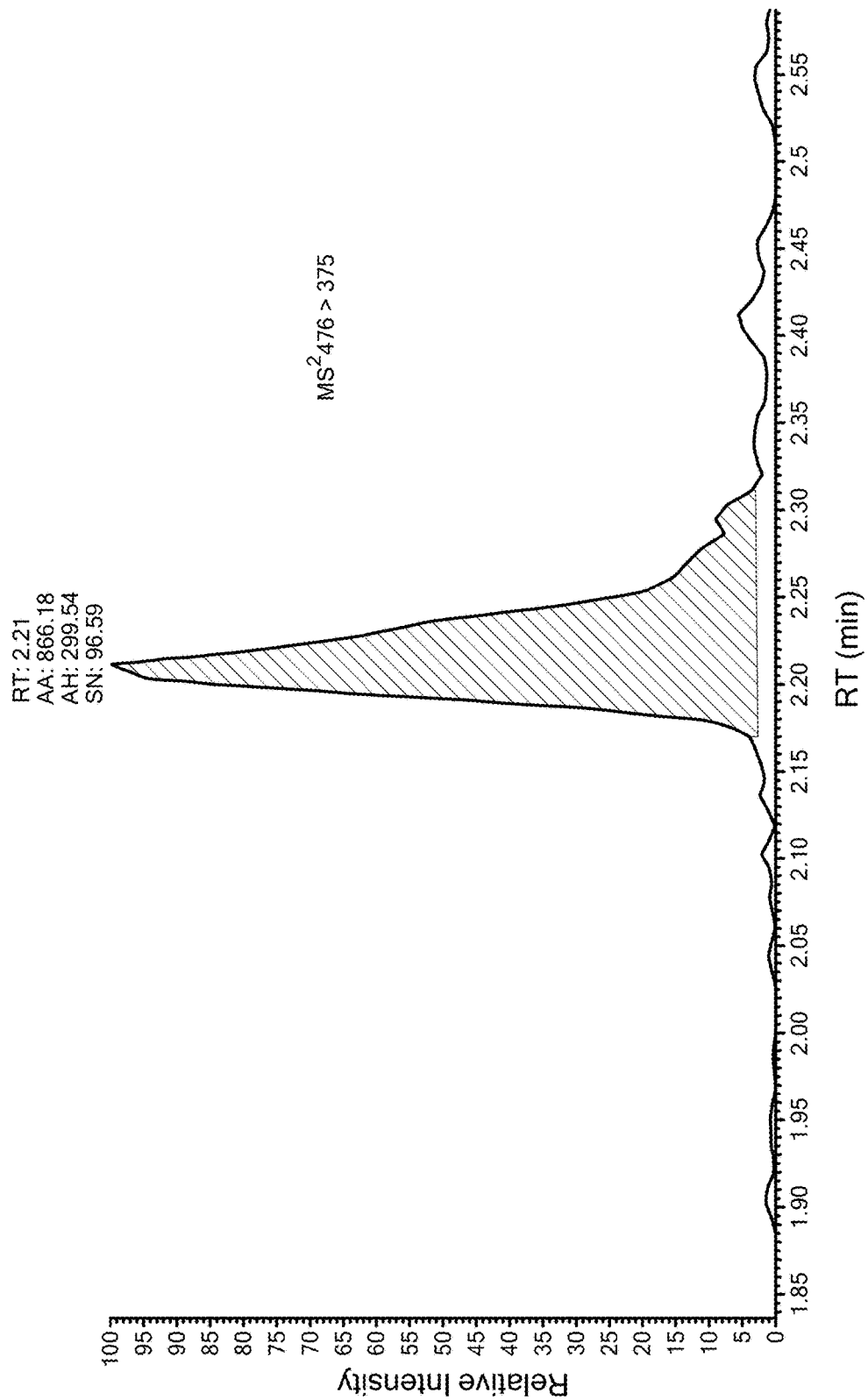
FIGS. 5A-5C show detection of 140 amol of TEBX-estradiol by HPLC-LTQ-MS.
Figure 5B:
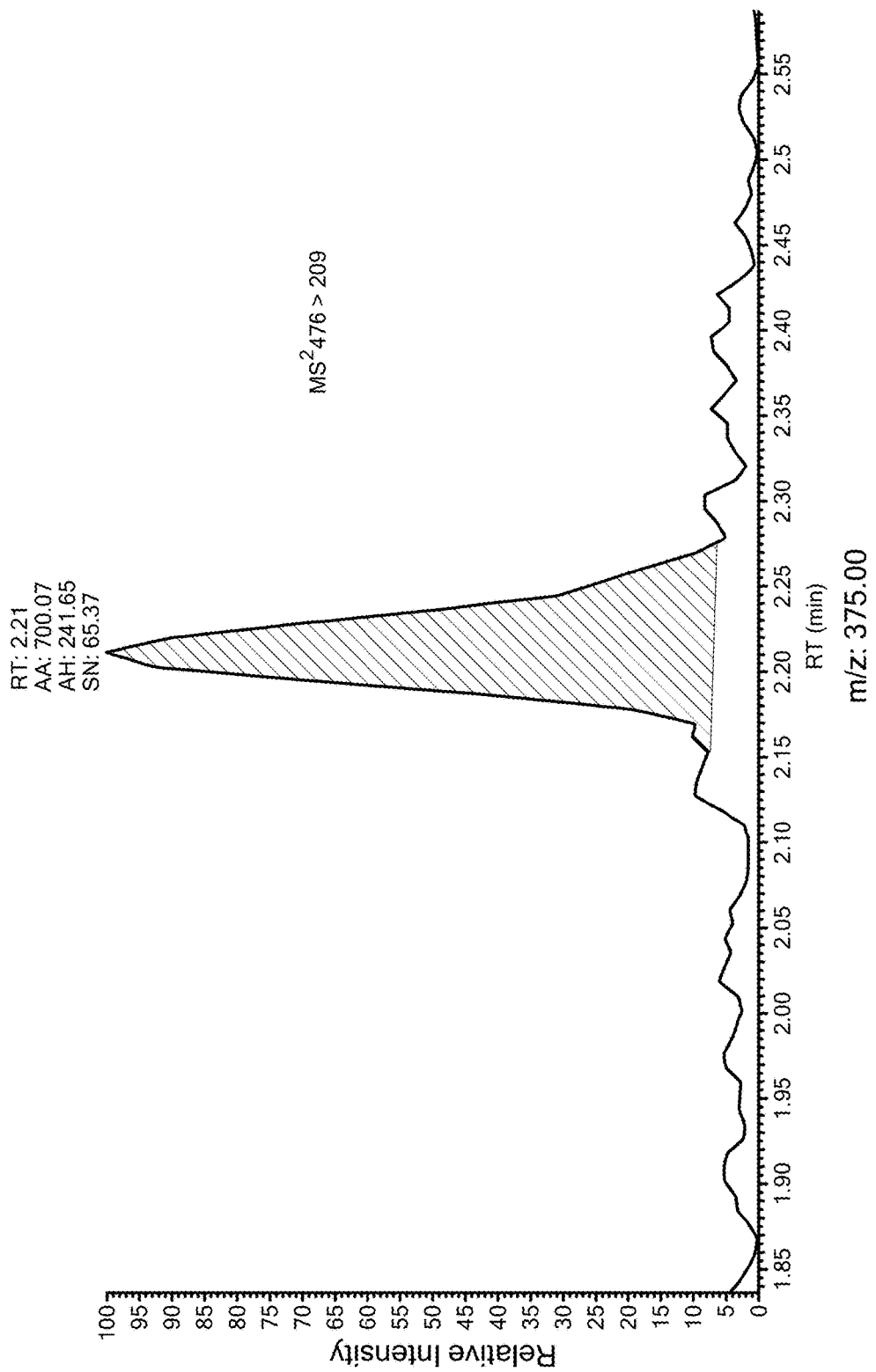
Figure 5C:
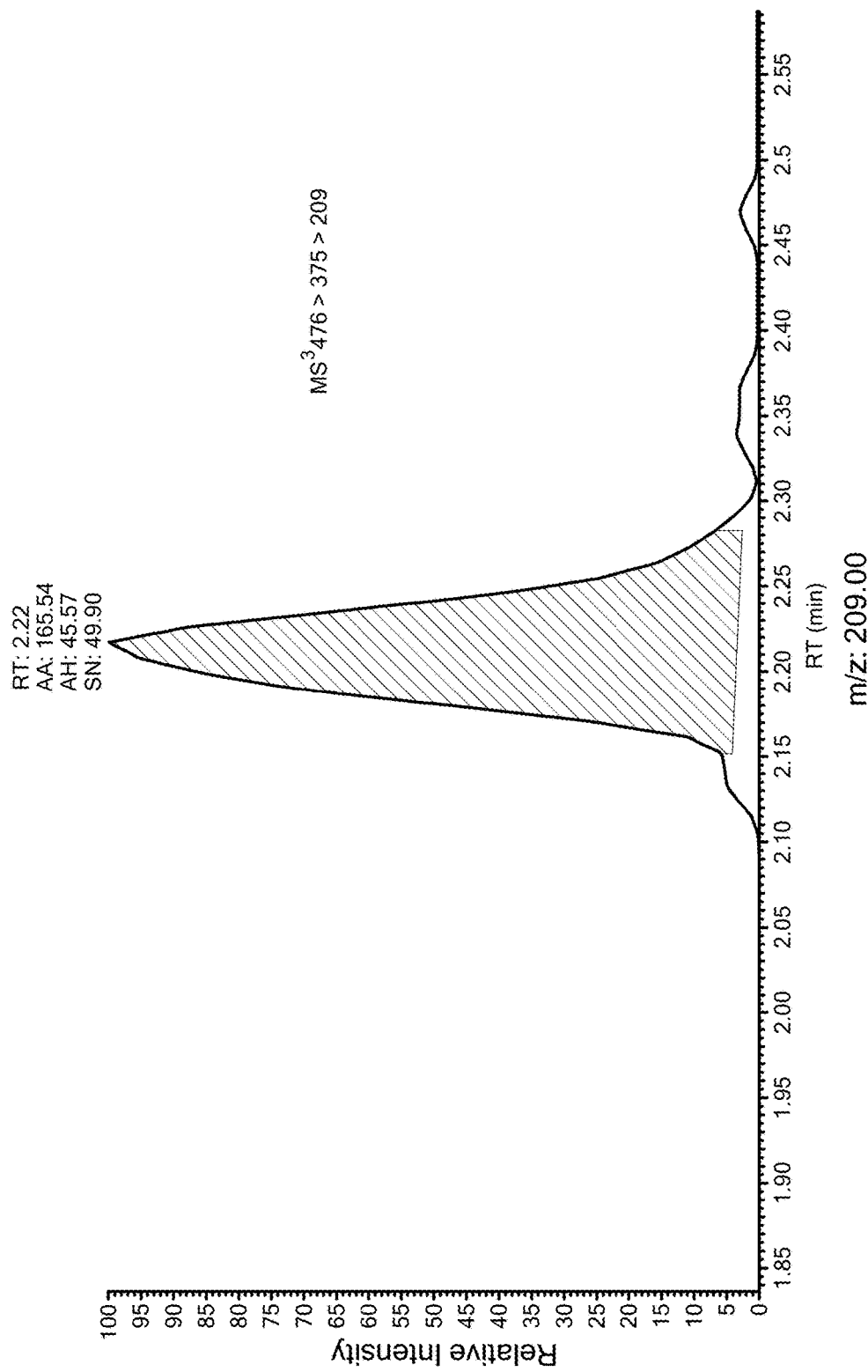

ACN over 40 min. The eluted sample was collected in a 8 to 17 min time window. The dried sample was re-injected into a nano-LC (Eksigent Tempo LC MALDI system, Dionex PepMap 100 C18 column, 0.075×150 mm, 3 µm) at 300 nL/min flow using a gradient from 12 to 90% ACN with 0.1% TFA over 50 min, and collected at 3 droplets/min onto a MALDI plate (CCA matrix: 2.5 mg/mL, 0.5 mL/min syringe pump flow). Subsequently, MALDI-TOF/TOF-MS was performed. FIG. 4A shows the MS detection result, and FIG. 4B shows the fragmentation pattern of TEBX-thymidine.

This application claims the priority of U.S. Provisional Application No. 62/110,008 filed 30 Jan. 2015 and entitled "Cation Tags for Attomole Detection by Mass Spectrometry", and U.S. Provisional Application No. 62/111,987 filed 4 Feb. 2015 and entitled "Cation Tags for Attomole Detection by Mass Spectrometry", the whole of which are hereby incorporated by reference.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. A method for detecting an analyte A using a multi-stage mass spectrometer having at least first and second stages, the method comprising the steps of:
   (a) contacting a sample containing the analyte with a molecular tag $Q^+$, whereby the analyte is covalently labeled with the molecular tag to produce tagged analyte $Q^+$-A,
   wherein $Q^+$ is represented by Formula (II)

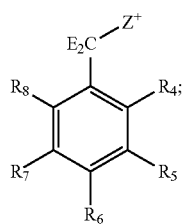

wherein $Z^+$ is selected from the group consisting of pyridinium, fluorine-substituted pyridinium, methoxy-substituted pyridinium, quinolinium, and triphenylphosphonium, and each E is independently hydrogen or deuterium;
   wherein one of $R_4$-$R_8$ bears a reactivity group that enables $Q^+$ to be attached covalently to the analyte to form $Q^+$-A, wherein the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof; wherein each $CE_2COCE_3$, $CE_2CONE_2$, $CE_2NHCOCE_3$, $CE_2OG$, $CE_2SG$, OG and SG is ortho or para to the $CE_2Z^+$ substituent;
   wherein $Q^+$-A comprises at least one O, N or S atom, provided by the analyte, which is separated from the C atom of the $CE_2Z^+$ substituent by three, four or five single or double bonds, and the O, N, or S atom is in a group which is ortho to the $CE_2Z$ substituent;
   (b) subjecting $Q^+$-A to volatization into the gas phase and then filtration in the first stage;
   (c) subjecting $Q^+$-A to cleavage by energetic activation to form a resonance-stabilized first product ion $q^+$-A and a neutral amine, wherein $q^+$ and the neutral amine are both fragments of $Q^+$;
   (d) filtering $q^+$-A in the second stage; and
   (e) detecting $q^+$-A.

2. The method of claim 1, wherein $Q^+$-A after filtration in the first stage but prior to filtration in the second stage undergoes two cleavages to form $q^+$-A' which is then filtered and detected.

3. The method of claim 1, wherein the reactivity group of $Q^+$ is selected from the group consisting of $CH_2X$, wherein X is Cl, Br, or I; $CH_2OH$; $CH_2SH$; $CH_2I$, $CH_2NH_2$; $CH_2NHNH_2$; $CH_2OSO_2C_6H_4CH_3$, $CH_2OSO_2CF_3$, $CH_2$-(2-oxy-N-methylpyridinium), $C_6H_4NH_2$, $CH_2OC_6H_4NH_2$, $CH_2OCH_2C_6H_4CH_2NH_2$, CHO; $CH_2OC_6H_4SO_2Cl$, $CH_2OCH_2C_6H_4SO_2NHNH_2$, $CH_2ONH_2$; $CH_2OC_6H_4NO$, $CH_2N_3$, $CH_2COCl$, COCl, $CH_2NCOCH_2Br$, $CONHNH_2$; $CH_2CHO$; $CH_2CONHNH_2$, $CH_2NCS$; $CH_2CO_2H$, $C_6H_4CO_2H$, $CH_2C_6H_4CO_2H$, $CO_2H$, $CH_2OC_6H_4CO_2H$, and $CH_2OCH_2CO_2H$.

4. The method of claim 3, wherein the reactivity group of $Q^+$ is $CH_2Br$.

5. The method of claim 1, wherein the total number of said N, O, or S atoms is 2.

6. The method of claim 1, wherein the total number of said N, O or S atoms is 3.

7. The method of claim 1, wherein $R_5$ or $R_6$ bears said reactivity group and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG.

8. The method of claim 1, wherein the sample is of environmental or biological origin.

9. A method for detecting an analyte A using a multi-stage mass spectrometer having at least first and second stages, the method comprising the steps of:
   (a) contacting a sample containing the analyte with a molecular tag $Q^+$, whereby the analyte is covalently labeled with the molecular tag to produce tagged analyte $Q^+$-A,
   wherein $Q^+$ is represented by Formula (II)

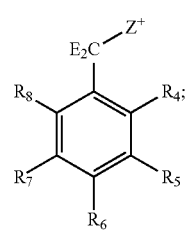

wherein $Z^+$ is selected from the group consisting of pyridinium, fluorine-substituted pyridinium, methoxy-substituted pyridinium, quinolinium, and triphenylphosphonium, and each E is independently hydrogen or deuterium;

wherein one of $R_4$-$R_8$ bears a reactivity group that enables $Q^+$ to be attached covalently to the analyte to form $Q^+$-A, wherein the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof; wherein each $CE_2COCE_3$, $CE_2CONE_2$, $CE_2NHCOCE_3$, $CE_2OG$, $CE_2SG$, OG and SG is ortho or para to the $CE_2Z^+$ substituent;

wherein $Q^+$-A comprises at least one O, N or S atom, provided by the analyte, which is separated from the C atom of the $CE_2Z^+$ substituent by three, four or five single or double bonds, and the O, N, or S atom is in a group which is ortho to the $CE_2Z$ substituent;

(b) subjecting $Q^+$-A to volatization into the gas phase and then filtration in the first stage;

(c) subjecting $Q^+$-A to cleavage by energetic activation to form a resonance-stabilized first product ion $q^+$-A and a neutral amine, wherein $q^+$ and the neutral amine are both fragments of $Q^+$;

(d) filtering $q^+$-A in the second stage;

(e) subjecting $q^+$-A to cleavage by energetic activation to form a second product ion $q^+$-A', wherein A' is a fragment of A;

(f) filtering $q^+$-A', and (g) detecting $q^+$-A'.

10. The method of claim 9, wherein the reactivity group of $Q^+$ is selected from the group consisting of $CH_2X$, wherein X is Cl, Br, or I; $CH_2OH$; $CH_2SH$; $CH_2I$, $CH_2NH_2$; $CH_2NHNH_2$; $CH_2OSO_2C_6H_4CH_3$, $CH_2OSO_2CF_3$, $CH_2$-(2-oxy-N-methylpyridinium), $C_6H_4NH_2$, $CH_2OC_6H_4NH_2$, $CH_2OCH_2C_6H_4CH_2NH_2$, CHO; $CH_2OC_6H_4SO_2Cl$, $CH_2OCH_2C_6H_4SO_2NHNH_2$, $CH_2ONH_2$; $CH_2OC_6H_4NO$, $CH_2N_3$, $CH_2COCl$, COCl, $CH_2NCOCH_2Br$, $CONHNH_2$; $CH_2CHO$; $CH_2CONHNH_2$, $CH_2NCS$; $CH_2CO_2H$, $C_6H_4CO_2H$, $CH_2C_6H_4CO_2H$, $CO_2H$, $CH_2OC_6H_4CO_2H$, and $CH_2OCH_2CO_2H$.

11. The method of claim 10, wherein the reactivity group of $Q^+$ is $CH_2Br$.

12. The method of claim 9, wherein the total number of said N, O, or S atoms is 2.

13. The method of claim 9, wherein the total number of said N, O or S atoms is 3.

14. The method of claim 9, wherein $R_5$ or $R_6$ bears said reactivity group and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG.

15. The method of claim 9, wherein the sample is of environmental or biological origin.

16. A tagged analyte for identification of the analyte A by multi-stage mass spectrometry, the tagged analyte having a structure of $Q^+$-A, wherein molecular tag $Q^+$ has a structure defined according to Formula (II):

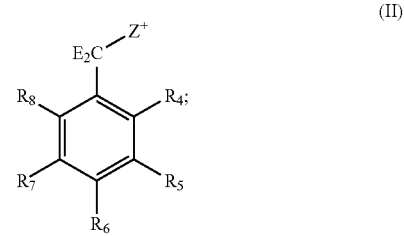

(II)

wherein $Z^+$ is selected from the group consisting of pyridinium, fluorine-substituted pyridinium, methoxy-substituted pyridinium, quinolinium, and triphenylphosphonium group, and each E is independently hydrogen or deuterium;

wherein one of $R_4$-$R_8$ bears a reactivity group that is used to covalently attach the molecular tag to the analyte;

wherein the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG, wherein G is methyl, ethyl, or propyl bearing H or D atoms, or a combination thereof; wherein each $CE_2COCE_3$, $CE_2CONE_2$, $CE_2NHCOCE_3$, $CE_2OG$, $CE_2SG$, OG and SG is ortho or para to the $CE_2Z^+$ substituent; and wherein $Q^+$-A comprises at least one O, N or S atom, provided by the analyte, which is separated from the C atom of the $CE_2Z^+$ substituent by three, four or five single or double bonds, and the O, N, or S atom is in a group which is ortho to the $CE_2Z^+$ substituent.

17. The tagged analyte of claim 16, wherein the reactivity group is selected from the group consisting of $CH_2X$, wherein X is Cl, Br, or I; $CH_2OH$; $CH_2SH$; $CH_2I$, $CH_2NH_2$; $CH_2NHNH_2$; $CH_2OSO_2C_6H_4CH_3$, $CH_2OSO_2CF_3$, $CH_2$-(2-oxy-N-methylpyridinium), $C_6H_4NH_2$, $CH_2OC_6H_4NH_2$, $CH_2OCH_2C_6H_4CH_2NH_2$, CHO; $CH_2OC_6H_4SO_2Cl$, $CH_2OCH_2C_6H_4SO_2NHNH_2$, $CH_2ONH_2$; $CH_2OC_6H_4NO$, $CH_2N_3$, $CH_2COCl$, COCl, $CH_2NCOCH_2Br$, $CONHNH_2$; $CH_2CHO$; $CH_2CONHNH_2$, $CH_2NCS$; $CH_2CO_2H$, $C_6H_4CO_2H$, $CH_2C_6H_4CO_2H$, $CO_2H$, $CH_2OC_6H_4CO_2H$, and $CH_2OCH_2CO_2H$.

18. The tagged analyte of claim 17, wherein the reactivity group is $CH_2Br$.

19. The tagged analyte of claim 16, wherein $R_5$ or $R_6$ bears said reactivity group and the remainder of $R_4$-$R_8$ are independently selected from H, D, $CE_2COCE_3$, $CE_2CONE_2$, $CE_2NHCOCE_3$, $CE_2OG$, $CE_2SG$, OG, and SG.

* * * * *